United States Patent [19]

Noll

[11] Patent Number: 5,446,538
[45] Date of Patent: Aug. 29, 1995

[54] PROCESS AND DEVICE FOR EMISSION SPECTORSCOPY

[75] Inventor: Reinhard Noll, Aachen, Germany

[73] Assignee: Fraunhofer-Gesellschaft zur Forderung der Angewandten Forschung E.V., Minich, Germany

[21] Appl. No.: 157,170

[22] PCT Filed: Jun. 2, 1992

[86] PCT No.: PCT/DE92/00447
§ 371 Date: Dec. 6, 1993
§ 102(e) Date: Dec. 6, 1993

[87] PCT Pub. No.: WO92/21957
PCT Pub. Date: Dec. 10, 1992

[30] Foreign Application Priority Data

Jun. 6, 1991 [DE] Germany .................... 4118518.8

[51] Int. Cl.$^6$ ............................................. G01N 21/63
[52] U.S. Cl. ................................................ 356/318
[58] Field of Search ........................................ 356/318

[56] References Cited

U.S. PATENT DOCUMENTS 4,645,342  2/1987  Tanimoto et al. ............ 356/318
4,839,493  6/1989  Herziger et al. ............ 219/121.69

FOREIGN PATENT DOCUMENTS 3413589  10/1985  Germany .
3720977   1/1989  Germany .

Primary Examiner—Vincent P. McGraw
Attorney, Agent, or Firm—Herbert Dubno

[57] ABSTRACT

Process for emission spectroscopy, particularly for laser emission spectroscopy, wherein the radiation emitted by the laser-induced plasma of the workpiece to be analyzed is decomposed by a spectrometer and at least one fraction of the found spectrum is transferred to a processing unit. In order to improve the process from the point of view of measurement precision and speed, it is carried out in such a manner that an influencing of the intensity of the plasma-inducing laser beam takes place depending on at least one emission-influencing parameter for the production of definite plasma states, this parameter being measured during plasma formation, and that the transfer of the found spectrum or of a fraction thereof to the processing unit is performed, as long as the measured plasma parameter is within a predetermined tolerance range ($T_I./.T_{II}$).

13 Claims, 8 Drawing Sheets

PROCESS AND DEVICE FOR EMISSION SPECTORSCOPY

CROSS REFERENCE TO RELATED APPLICATION

This application is a national phase of PCT/DE92/00447 filed 2 Jun. 1992 and based, in turn, upon German national application P41 18 518.8 filed 6 Jun. 1991 under the International Convention.

FIELD OF THE INVENTION

The invention relates to a process for emission spectroscopy, particularly laser emission spectroscopy, wherein the radiation emitted by the laser-induced plasma of the material to be analyzed is broken down by a spectrometer and at least one fraction of the found spectrum is transferred to a processing device for element analysis.

BACKGROUND OF THE INVENTION

Exemplified by laser emission spectroscopy and spark emission spectroscopy, emission spectroscopy serves for material analysis, whereby the laser beam or the sparks are used for the vaporization of minimal amounts of material, so that the vaporized material can be analyzed. According to FIG. 1A at (1) a laser beam is focussed on the workpiece to be analyzed. Based on the natural absorption of the laser beam by the workpiece 4 an energy coupling as per FIG. 1B occurs at 2 in a localized area, wherefrom a part of the material is vaporized according to FIG. 1A-1D, the vapor being seen at 3. The amount of the vaporized material depends on the energy, the output and the output density, the local output distribution and the wavelength of the laser beam. The generation and the state of the vaporized material are also influenced by the characteristics themselves and by the surrounding atmosphere.

The laser beam is coupled into the vaporized material, so that the latter is brought into a plasma state or a plasma-like state. As a result of the energy coupling, the components of the plasma are induced to emit radiation. The thereby emitted radiation 40 according to FIG. 1D is characteristic of the composition of the material to be analyzed.

The beam 40 emitted by the plasma 6 is directed towards a spectrometer and is there spectrally decomposed. For instance the dependency of the radiation intensity $I_S = f(\lambda)$ can be obtained as shown in FIG. 3. This information is fed to a processing unit, which for instance is equipped with a computer and an output device. In the processing unit, intensity, or line ratios, are calculated with the aid of calibrating curves, in order to determine the element concentration of the material. For instance a ratio between the intensity $I_1$ of an emission line $\lambda_1$ in relation to the intensity $I_2$ of an emission line $\lambda_2$ is established, whereby the emission line $\lambda_2$ serves as reference line and for instance originates from the element which is most often present in the examined material. With the aid of the ratio $I_1/I_2$ it is possible to determine in percentage the content $C_1$ of a first element of the entire material with the aid of a calibration curve $I_1/I_2 = f(C)$ according to FIG. 3a.

Such material analyses with laser beams are contactless methods, which can practically be carried out without sample taking. Being performed with fast components, they afford the possibility of high measuring speeds. Therefore they can be incorporated in processing and machining production lines, without impairing the flow of workpieces by taking samples and transporting the samples to the analyzing device. It is possible to perform elemental and multi-elemental analyses. Through on-line analysis, it is possible for instance to survey quantitatively and qualitatively the production processes of workpieces. Furthermore it is even possible to intervene in a controlled manner in the production of workpieces, when high measuring speeds make possible an on-line analysis. For instance it is possible to control the introduced raw materials, to test the identity of workpieces and to sort out mixed materials and workpieces. However these basic possibilities can be limited by the fact that accuracy of measurement and the reproducibility are low because the changes in the plasma state with time are not sufficiently considered. FIG. 2 illustrates the principle that $I = f(t)$ represents the timed interdependence between the path of the curve of the intensity of the laser beam and the path of the curve of the intensity of the plasma-emitted beam. For instance to a laser beam intensity of $I_{L1}(t)$ the intensity $I_{S1}(t)$ is supposed to correspond. It can be seen that the emitted radiation occurs with a delay, because the plasma has first to build up under the effect of the laser beam. If regarding the curve of its intensity the laser radiation behaved according to $I_{L2}(t)$, so for the intensity of the emitted plasma radiation a curve according to $I_{S2}(t)$ would result. The different intensity curves of the emitted radiation are explained by the fact that the temperature conditions responsible for the intensity of the emitted radiation undergo a delayed change, depending on the irradiating energy and thereby by the pulse course of the laser beam. For this reason it is important to establish precisely the time range or the particular moment in time $t_m$ for the measurement or the evaluation because only at that particular moment is the radiation emission optimal. Reference is made to FIGS. 4a to 4c, wherein the intensity curve $I_S = f(\lambda)$ is represented, and namely for the moments in time $t_a$, $t_m$ and $t_e$. At the moment $t_a$ the radiation intensity is relatively low, the same applying also to $I_{te}$ the moment $t_e$. This is in correspondence with $I_{S1}(t)$. It can be seen that the emission line is only weakly developed. By contrast the emission lines at the moment $t_m$ are optimally developed and the analyses according to FIGS. 3, and 3a can be carried out with maximal precision. However, in the known processes this is considered only to the extent that after the start of the laser pulse or of a discharge process triggering the laser pulse a fixed moment in time is established, so that different developments which the plasma undergoes in time are not taken into consideration. Therefore in the known devices the optimal point in time $t_m$ for different plasmae is not reached.

From DE-A-34 13 589 a device for laser emission spectroscopy is known, wherein a fraction of the radiation emitted by the material to be analyzed is directed to a photodiode, by means of which a reference signal is produced which is fed to a signal processor. Here the signal of the photodiode, which measures only the integral radiation intensity of the plasma, serves for the standardization of the signal spectrum found by the spectrograph. A different development of the plasmae over time, and therewith an increase of the accuracy of measurement, as well as a reduction of the measuring times does not take place.

From U.S. Pat. No. 4,690,558 a process for the laser emission spectroscopy is known, wherein the accuracy of the analysis is supposed to be enhanced due to the fact that GAUSS-distribution of the TEM$_{00}$-Mode is used. Further a measuring of the spectral intensity is supposed to be performed only when the intensity ratio of a pair of preselected spectral lines of the light emitted by the object to be examined lies within a predetermined range. Consequently the described accuracy errors are reduced, however there is no reduction in the measuring times. A way to influence the way the laser works is not described.

From WO-A-86/00552 a device for the processing of workpieces by means of laser beams is known, based on the buildup of a plasma to be kept within limits. The device has diagnostic means, which serve for the constant detection of the processes developing in the area where the workpiece is being processed and for the detection of plasma parameters. With these plasma parameters the laser intensity is kept within predetermined limits, in order to avoid a plasma detonation. A quantitative spectrographic analysis of the material does not take place.

OBJECT OF THE INVENTION

It is the object of the invention to improve a process of the aforementioned kind, so that the precision of measurement and reducibility, particularly for quantitative analyses are increased and that the measuring times are reduced.

SUMMARY OF THE INVENTION

This object is achieved by influencing the intensity of the plasma-inducing laser beam, for the purpose of producing defined plasma states, depending on at least one emission-influencing parameter, this parameter being measured during plasma formation. The detected spectrum or a fraction thereof is transferred to the processing unit when the measured plasma parameter lies within a predetermined tolerance range.

The concept that emission-influencing parameters, i.e. plasma parameters, have to be considered during the measuring process is important to the invention. At least one such plasma parameter has to be measured during plasma formation, so that the transfer of the detected spectrum to the processing unit can be carried out in relation to the result of measurement, so that the analysis can take place at the optimal moment in time $t_m$, based on a radiation emission according to FIG. 4b for different plasmas or for different plasma developments in time. This results in a comparatively high accuracy of measurement and reproducibility in a minimal number of laser-induced plasmas. Based on the reduced measuring times, the on-line application of the process in high-speed analyses can be taken into consideration, namely also in cases with a detection sensitivity in the ppm-range.

Since the plasma parameter is set in relation to a certain predetermined tolerance range, it is possible to coordinate the process with the different element properties of the material to be analyzed, for instance with different vaporization temperatures of the elements of the material. For instance it could be taken into consideration that, while a first element of the material has already a radiation emission according to FIG. 4b, so that the desired analysis can be performed under optimal conditions, a second element of the material has not yet reached this point, but for instance emits first a radiation according to FIG. 4a, because it has a higher vaporization temperature. By using the same laser-induced plasma, the process could correspondingly be carried out in such a manner that the first element be analyzed at an instant in time $t_{m1}$ and the second element at an instant in time $t_{m2}$, each of them being analyzed at the optimal moment. Thus a multiple analysis in a short time is possible with the process, wherein the detection sensitivity for the separate elements is optimal. The process can therefore extend to the ppm-range required for secondary metallurgy.

The economic importance of the process according to the invention resides in the fact that a multiple elemental analysis in the production of steel is even today performed through sample taking, whereby the sample has to be transported and analyzed after cooling, so that correspondingly delays of minutes result, leading to corresponding energy losses due to the heating of large amounts of melt.

Besides it is an advantage of the process of the invention that it is not limited to a single plasma parameter, but that basically all plasma parameters which are important for the beam emission can be considered in this process. Furthermore, a lower sensitivity of the process to changes in focussing, in the laser beam and in the surrounding conditions results.

Of particular importance as an emission-influencing parameter is the temperature of the plasma. Correspondingly, the process is carried out so that the plasma temperature is used as the plasma parameter.

The laser-induced plasma can for instance have different densities, depending on the composition of the material and the ambient pressure, which in turn influences the emitted radiation. Therefore in a further development of the invention, the process is carried out so that, in addition to the plasma temperature, the plasma density is also used as a parameter.

In order to adjust the process to different analyzing tasks, it is carried out so that the maximal value of one parameter of a pulse-induced plasma is measured, this maximal value is compared as an actual value with a target value range (set-point value), and that the energy of the subsequent laser pulse is increased or lowered when the maximal value lies below or above the target value range. With a precision corresponding to the target value range a defined state of the induced plasma can be achieved, whereby the radiation emitted by this plasma can be evaluated in a reproducible manner.

Furthermore the process can also be carried out so that a continuous measuring of a parameter curve of pulse-induced plasma takes place, that this real parameter curve is continuously compared with a target parameter curve, and that in case of deviations adjustment values determined by the differences are produced and are involved in the continuous adjustment of the laser-beam energy during pulse generation. Such a control of the laser-beam energy makes possible a further improvement of the process in the sense of achieving defined plasma states.

In the aforedescribed control process, as well as in the aforedescribed adjustment process, adjustments of the process to the material to be analyzed, in order to optimize the measurement results can be achieved in that the target value range and/or the target parameter curve is specifically predetermined for an element or for a group of elements to be analyzed.

In order to obtain the best possible analysis results, radiation emitted from the same source area of the plasma is fed to the spectrometer and to the parameter sensor.

As a result of the increased accuracy of measurement and the considerable measuring speed, a process control of the pertaining workpiece can take place based on the result of the elemental analysis depending on plasma parameters.

The process can be carried out so that the emission intensity of a number of preselected emission lines and also at least one plasma parameter are recorded in a time-dependent fashion, before the transfer to the processing installation depending on the preselected tolerance range. Therefore it is not required to detect and evaluate the entire spectrum at a certain moment in time or within a short time interval, but preselected emission lines, namely the ones of interest to the analysis, can be detected over the entire course of the plasma formation. In this way it is insured that for these emission lines all plasma states which can be evaluated are detected, including those wherein the plasma parameter is within the predetermined tolerance range.

The invention also relates to a device for carrying out the process. From DE-A-34 13 589 a device is known, wherein in the beam path of the laser beam a laser-beam permeable shielding mirror stopping the radiation emitted by the plasma is arranged and optically connected to a spectrometer, as well as to a plasma-parameter sensor. In order to improve this device in the spirit of the above-stated object of the invention, i.e. in order to increase the accuracy of measurement and to reduce the measuring times, this device is further developed so that a lens system surveying the plasma is provided, which is connected to the spectrometer via a light waveguide and that as plasma-parameter sensor a plasma-temperature sensor and/or a plasma-density sensor is available. With the aforementioned features a device can be further developed in the spirit of the above-stated object of the invention, even then when it has the features known from DE-A-34 13 589, namely according to which in the device a spectrometer is connected with a lens system receiving the radiation emitted by the plasma and in whose beam path a plasma-parameter sensor is coupled in over a mirror. Due to both devices it can be achieved that the plasma can be optimally observed, particularly with respect to the same source area.

In order to obtain defined plasma states for the evaluation of the measurement results, the device is designed so that the plasma-parameter sensor is connected to a laser control and adjustment unit, which receives predetermined values of the target value range and of the parameter curves from a central unit.

Especially for the evaluation of the entire detected spectrum, the device is designed so that the plasma-parameter sensor is connected to a reference unit which incorporates predetermined values of the tolerance range received from a central unit and with which a transfer unit arranged between the spectrometer and the processing device can be controlled.

The evaluation of one or more emission lines of the found spectrum is made possible due to the fact that the plasma-parameter sensor is connected to a memory coupled with the spectrometer via a slot diaphragm, with a subsequently arranged discrete detecting unit tuned to detect a single emission line or a background signal of the spectrum and which stands in a transfer connection with the processing device which receives the predetermined values of the tolerance range from the central unit.

BRIEF DESCRIPTION OF THE DRAWING

The above and other objects, features, and advantages will become more readily apparent from the following description, reference being made to the accompanying drawing in which.

SPECIFIC DESCRIPTION

Figure 1A:
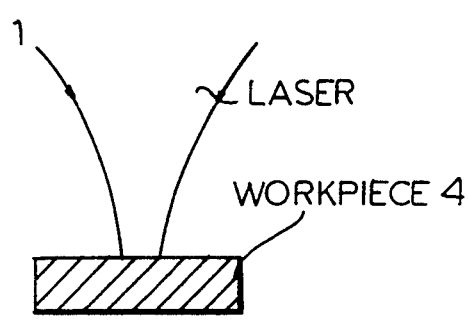
FIGS. 1A–1D are diagrams illustrating the development of laser-induced plasma radiation.
Figure 1B:
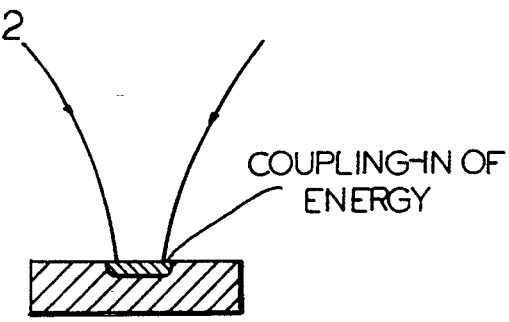
Figure 1C:
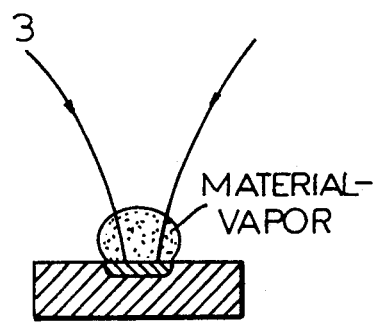
Figure 1D:
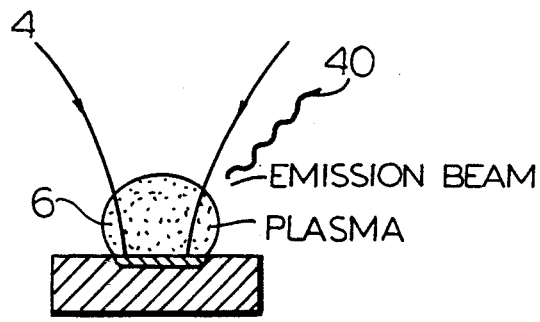
Figure 2:
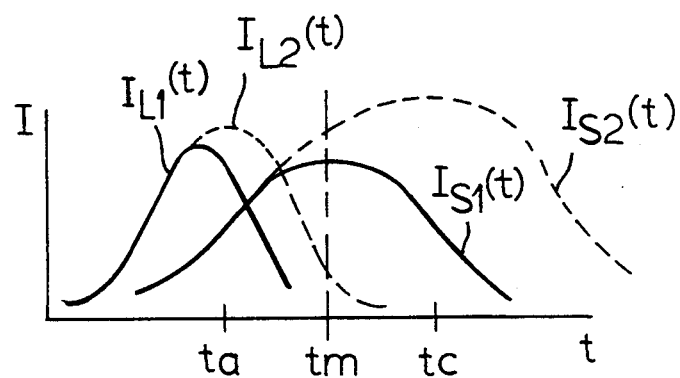
FIG. 2 is a diagrammatic representation $I = f(t)$ for the intensity curve in a laser pulse and a pulse-induced plasma.
Figure 3:
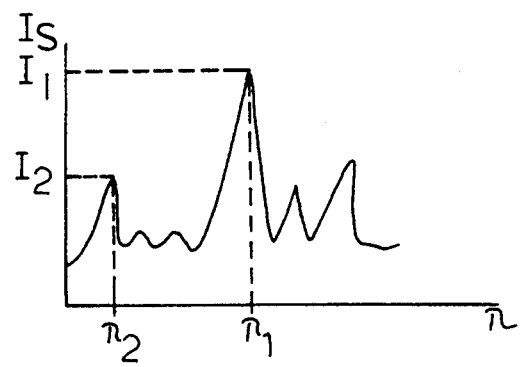
FIG. 3 is a graph showing a curve of the intensity $I_S = f(\lambda)$ for a material.
Figure 3A:
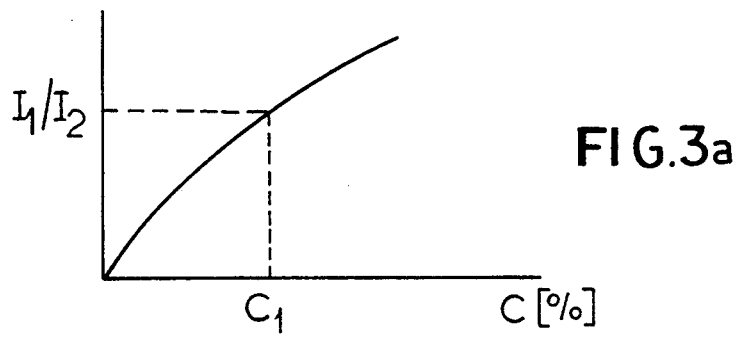
FIG. 3a a calibration curve for the intensity graph of FIG. 3.
Figure 4A:
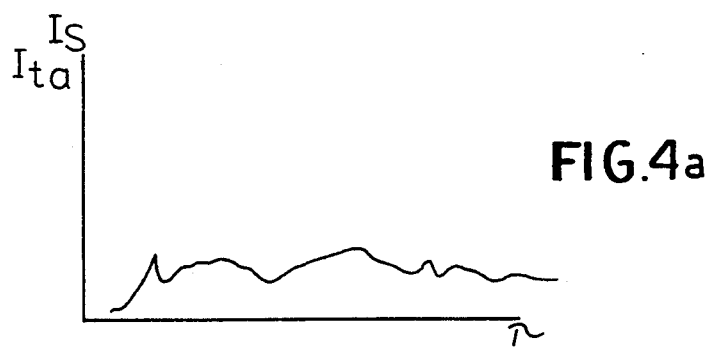
FIGS. 4a to 4c are diagrammatic curves $I_S = f(\lambda)$ for different moments in time in pulsewise laser-induced plasma.
Figure 4B:
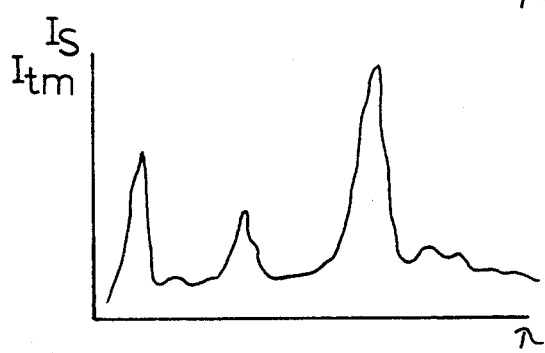
Figure 4C:
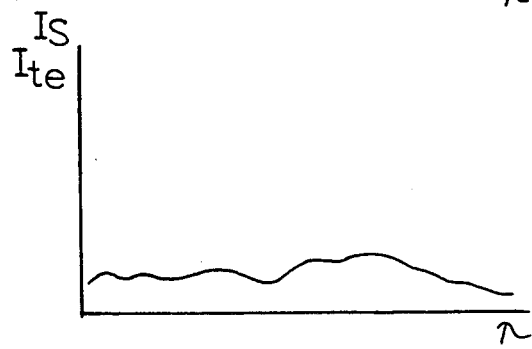
Figure 5:
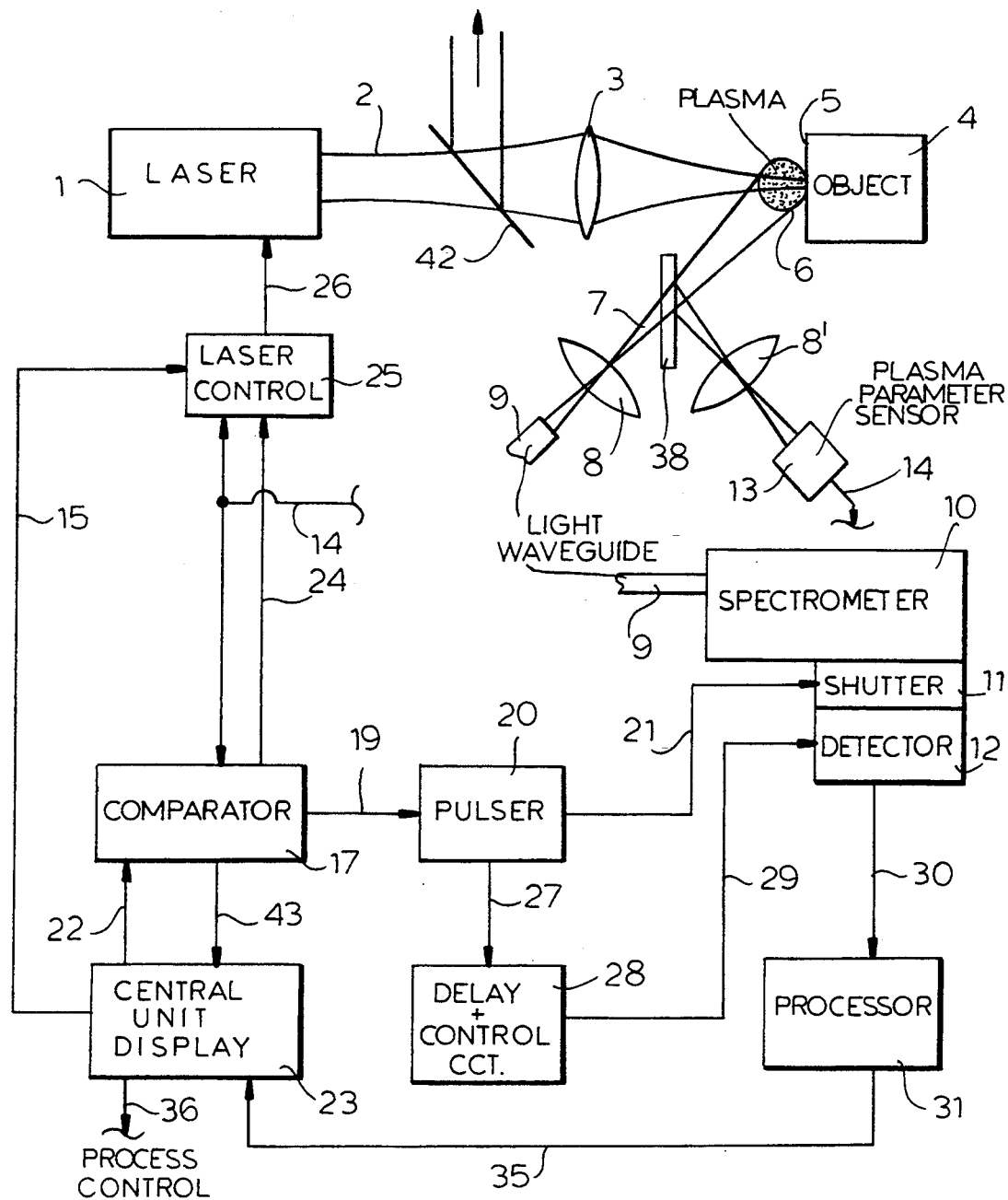
FIG. 5 is a schematic representation of a device for the laser emission spectroscopy in connection with a block diagram describing the functional flow.

According to FIG. 5, an object 4 to be measured is irradiated by a laser 1 with a laser beam 2, which is focussed by an optical system 3. On the surface of object 4 to be measured a plasma 6 is formed, which is observed by means of a lens system 8, so that the radiation 40 emitted according to FIGS. 1A–1D is guided as light along the beam path 7 to a light waveguide 9, which directs the light towards a spectrometer 10. The spectrum decomposed in spectrometer 10 is recorded with a detector 12, with the interposition of an electro-optical shutter 11. The shutter 11 and the detector 12 form a controllable transfer unit. The detector 12 is connected to a processing device 31 via a lead 30. The data collected from the detector 12 are digitalized in the processing unit and the spectra are processed in the usual manner for the quantitative element analysis. The results of the processing unit 31 are further directed via connection 35 to the central unit 23, which for instance as a display device, or which via a lead 36 delivers for instance information for process control, which can have an effect on the further processing of the object 4 to be measured. This object 4 to be measured can be any object, provided that plasma can be induced therein with a laser beam 2. Therefore the object 4 to be measured can be a gas, a vapor, a solid body or a liquid. In the beam path 7 of the lens system 8 a partially transparent mirror 38 is coupled in, by means of which a fraction of the light emitted by the plasma 6 can be directed with a lens system 8' to a plasma-parameter sensor 13. This sensor 13 or the lens system 8 can also be acted upon via a shielding mirror 42 by the radiation 40 emitted by plasma 6, which returns via laser lens system 3 to the shielding mirror 42, which can be traversed by the laser beam 2. In both cases the sensor 13 is subjected to the beam 40 emitted by the same source area of plasma 6. A temperature sensor can be used for instance as a sensor for detecting a plasma parameter, which delivers a temperature signal T(t) of plasma 6. The temperature sensor is for instance designed so that two wave lengths of an element of the object to be measured are filtered out from the received plasma light and the respective radiation is recorded by a detector. The signals recorded by the detector are set in a ratio and are corrected in reference to the characteristic curves. In this way an adjustment of the sensor to the measuring task can be achieved, for instance to determine quantitatively a certain element of object to be measured. In addition, the temperature sensor is designed suitably so that it can follow the typical change times of a laser-induced plasma.

Figure 6:
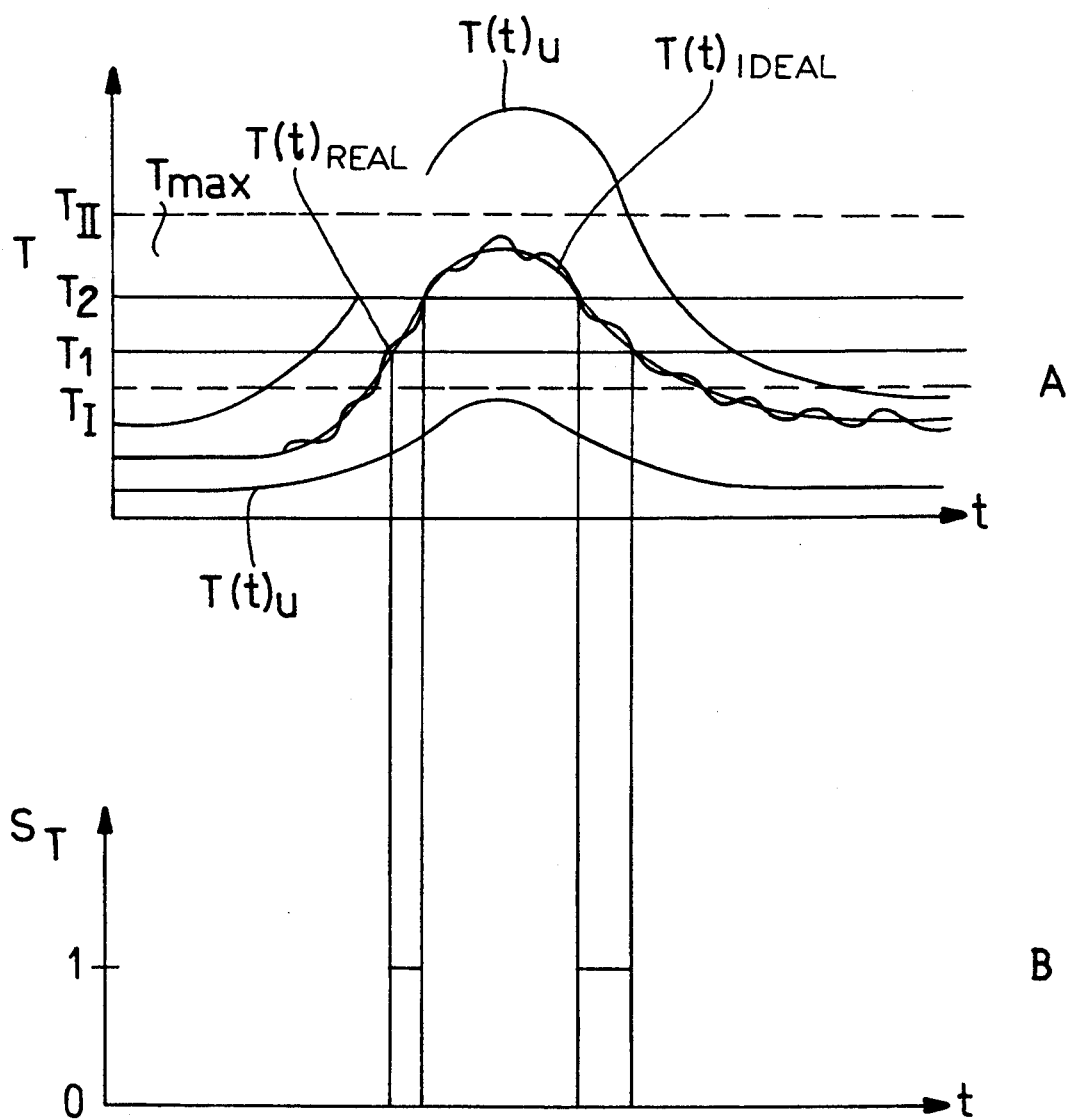
FIG. 6 is a diagram showing in part A the diagrammatic dependence of the plasma parameter of temperature $T = f(t)$ for the control of the transfer of the found spectrum to the processing device and in part B a graph of $S_t$VS. time.

The temperature signal T(t) detected by sensor 13 is fed via a lead 14 to a laser control and adjustment unit 25 on the one hand, and on the other hand to a comparison unit 17. FIG. 6 shows at A T=f(t) with various T(t) curves. Each curve is initiated by a laser pulse. The curve T(t)$_u$ shows a relatively flat salient of the temperature curve, while T(t)$_{ii}$ shows a very significant salient. It can now be determined that $T_{max}$ as a maximal temperature has to be within a target value range of $T_I$ to $T_{II}$, so that an orderly measurement can be performed. Consequently with the assistance of the laser control and adjustment unit 25 it can be insured that the maximal value $T_{max}$ will vary within a a target value range $T_I/T_{II}$, by performing a comparison and by influencing the energy of laser beam 2 to correspond with the result of the comparison, for which purpose the unit 25 acts via a lead 26 upon the laser 1 and there for instance correspondingly changes the supply voltage of the bank of capacitors. The change takes place so that for the next laser pulse the energy of the laser beam is increased by a value to be predetermined when $T_{max} < T_I$. In case $T_{max} > T_{II}$, the energy of the laser beam for the next pulse is reduced by a value to be predetermined. For $T_I < T_{max} < T_{II}$ for the next pulse the same energy for the laser beam 2 is selected. In order to achieve a more rapid control, it is also possible to follow laser strategies in laser pulse sequences which allow for a quick adjustment to the required laser pulse energy.

The data for the target value range $T_I/T_{II}$ are fed via a lead 26 to the unit 25 for the measuring processes i=1, 2 ... N from the central unit 23 where they are available as preprogrammed and are picked up depending for instance on the clock sequence of the measuring results of sensor 13 over the comparison unit 17 and a clock pulse lead 43 to the central unit 23.

The control and adjustment unit 25 can also be be used in a different way in order to enforce definite plasma states. In FIG. 6, part A, an ideal parameter curve T(t)$_{ideal}$ is represented, which should be reached as accurately as possible, for the further described reasons. Therefor the effective curve T(t)$_{real}$ found by sensor 13 is established and compared with the curve T(t)$_{ideal}$ to be given by the central unit 23. Corresponding to this comparison, in the case when T(t)$_{real}$−T(t)$_{ideal}$ does not equal zero, a control value is generated which influences the laser beam curve in such a way that the actual temperature curve T(t)$_{real}$ in the plasma adjusts itself as much as possible to the target curve T(t)$_{ideal}$. Consequently while in the case of the laser control the subsequently measured pulse is influenced, in the laser adjustment the very same pulse which determines the measurement result is changed to the required extent during its course. The change takes place for instance by means of an internal resonator quality modulation within a flash lamp discharge.

After it has been described how it can be achieved that T(t) follows a certain curve, so that consequently by using a certain emission-influencing parameter a definite plasma state can be reached, it is further described how the transfer of the spectrum found by the spectrometer 10 to the processing unit 31 can be influenced. Thereby it is presumed that the point in time for the transfer has come when the respective emission spectrum of the laser-induced plasma is within a predetermined tolerance range of the continuously measured plasma parameters, for instance within a predetermined temperature range $T_1./.T_2$. Then for the case $T_1 < T, T_2$ it can be established, for instance in a calibrating phase, that the respective emission spectrum is particularly suited to the quantitative concentration definition of an element or a group of elements. This tolerance range $T_1./.T_2$ is represented in FIG. 6, part A. During measuring the comparison unit 17 receives from the central unit 23 via lead 22 the control signal of this tolerance range $T_1./.T_2$ and can in this way, by evaluating the measurement result, generate a signal $S_T$, represented in FIG. 6, part B. This signal $S_T$ is directed via lead 19 to a pulsator 20 which opens or closes the electro-optical shutter 11 depending on the state of the signal S(t). By means of the pulsator 20 at the same time a delay and control unit 28 is triggered, which over lead 29 influences the sorting process of the detector 12. The delay follows the system-inherent delays, which are primarily conditioned by the electro-optical shutter 11.

From FIG. 6, part B it can be seen that the emission-influencing parameter, namely the temperature, finds itself twice within the predetermined tolerance range $T_1./.T_2$ in the course of a temperature curve T(t). In this way, during a single pulse-induced curve T(t) in a single plasma, two transfers of the detected spectrum to the processing unit 31 can be performed, a fact which increases the precision relative to a single testing process.

The radiation emitted by the plasma depends also on other plasma parameters besides the temperature, for instance the time-dependent curve of density N(t) and/or the time-dependent formation of the plasma geometry. Such plasma parameters can be detected by corresponding sensors, the density for instance with a density sensor which is designed as an interferometer, or by finding spectroscopically the width of the emission lines, which also depends on plasma density.

Figure 7:
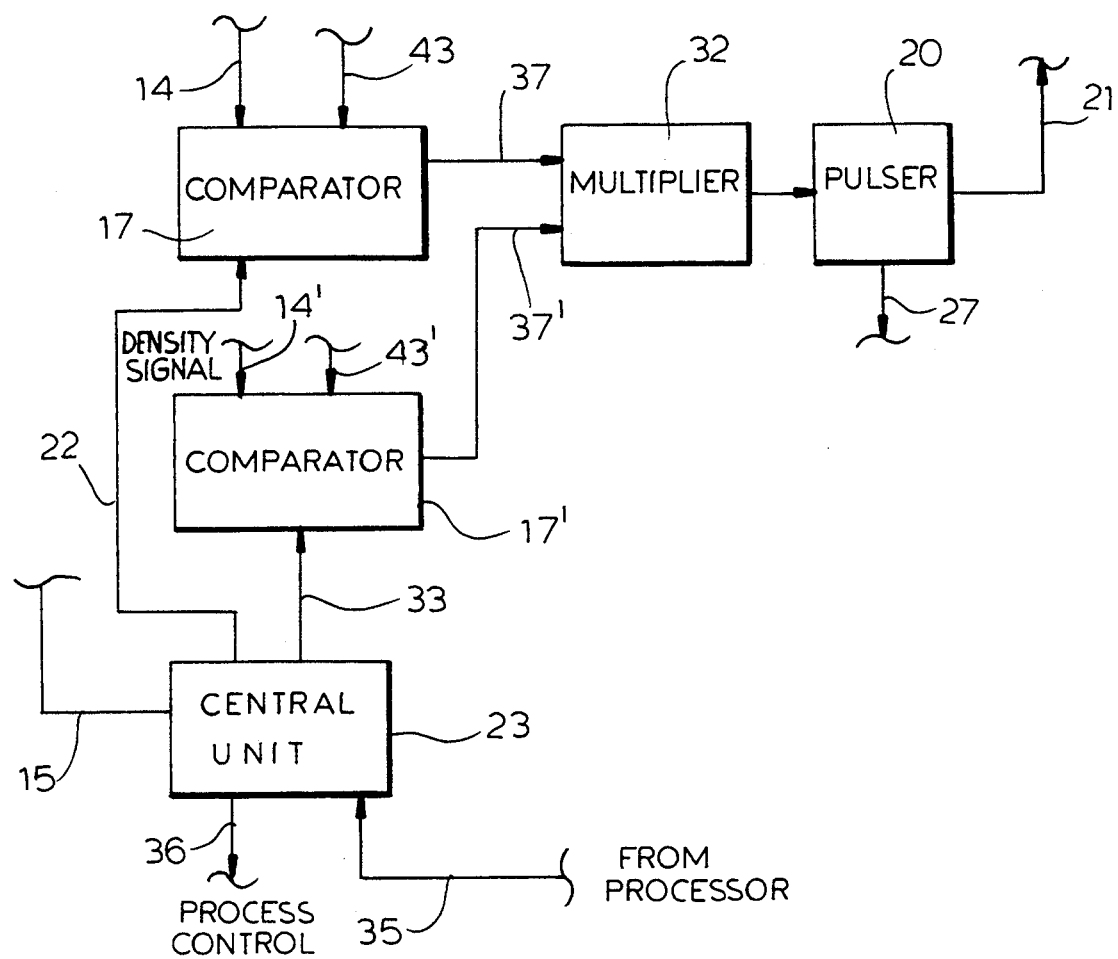
FIG. 7 is an addition to block diagram of FIG. 5 for the case when a second plasma parameter is taken into consideration in the control of the transfer of the found spectrum to the processing device.
Figure 8:
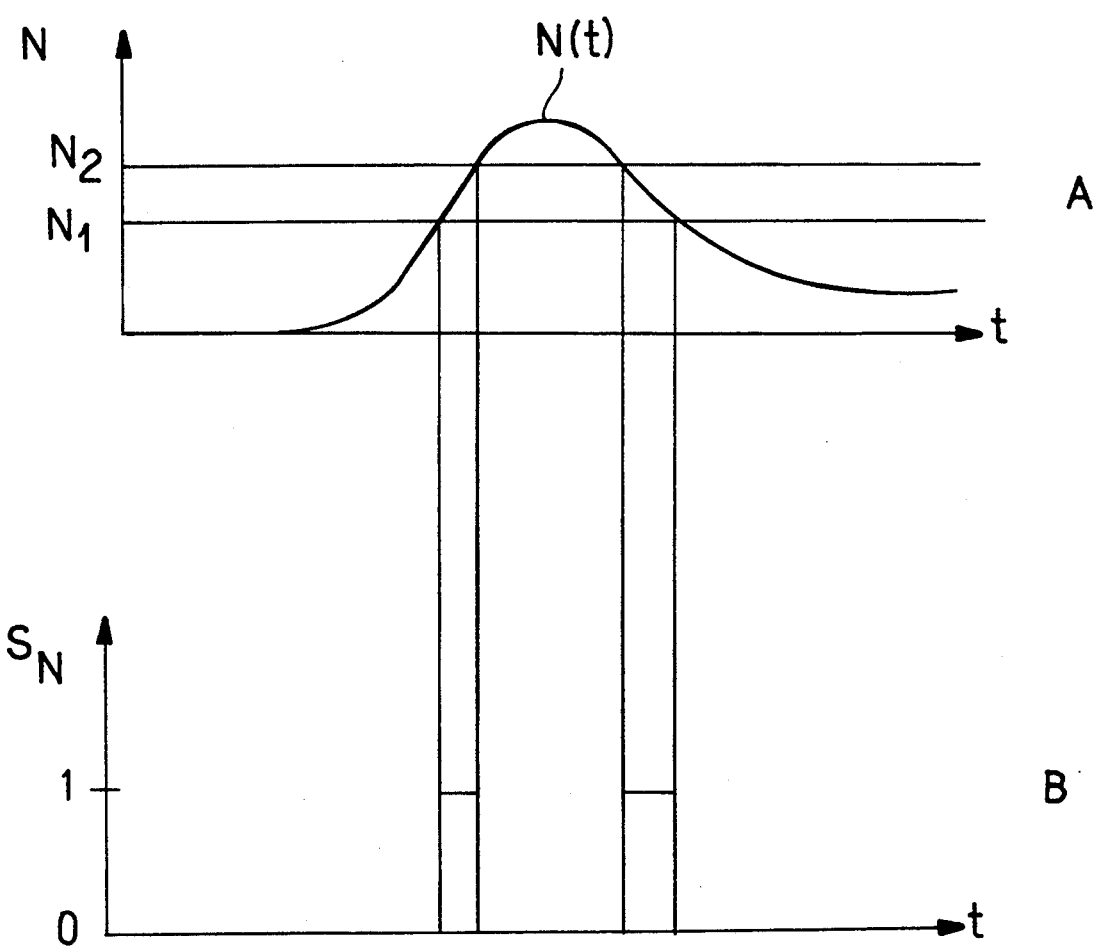
FIG. 8 is a diagram similar to FIG. 6 of the timed-conditioned curves $N-f(t)$ and $S_N = f(t)$ for the plasma density $N(t)$ as a second plasma parameter.
Figure 9:
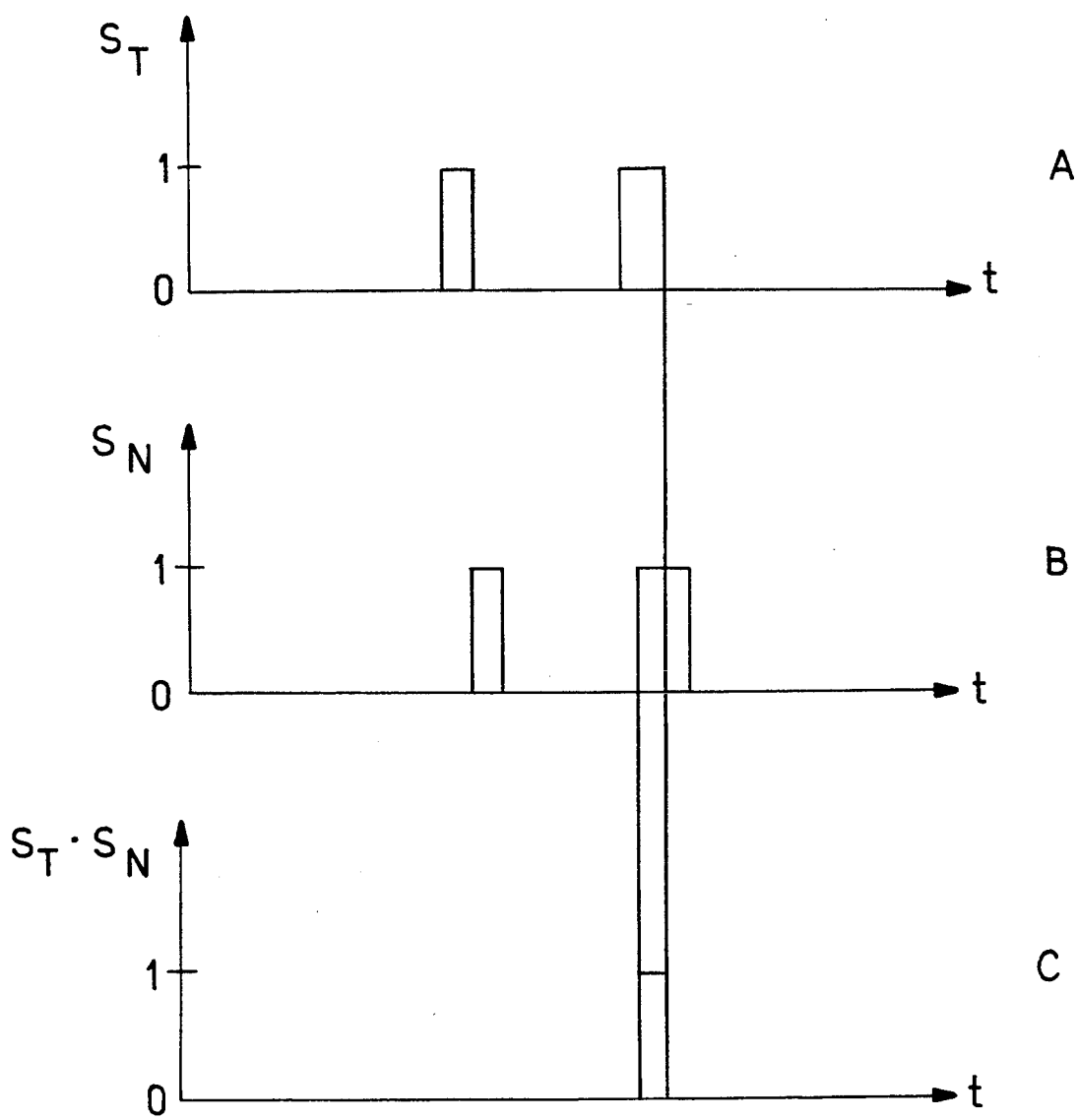
FIG. 9 is an illustration for the clarification of the control of the transfer of the detected spectrum to the processing unit depending on both plasma parameters $T(t)$ and $N(t)$.

FIG. 7 shows a block diagram embodiment of a device, which also takes into account the additional curve N(t). Therefore an additional comparison unit 17' is provided, which receives the density signal over a lead 14' which for instance is a branch lead of lead 14. The curve N(t) is represented in FIG. 8, part A. By analogy to FIG. 6, a predetermined tolerance range $N_1./.N_2$ is taken into account for the testing, for which purpose the comparison unit 17' receives the respective limiting values $N_1$, $N_2$ from the central unit 23 via lead 33. As long as the plasma has a density within this tolerance range $N_1./.N_2$, a signal $S_N$ is generated, in the present case twice during the a single laser pulse. This signal $S_N$ is directed via a lead 37 to a multiplier 32, which according to FIG. 9, part C produces an output signal, when there is a signal $S_T$ according to FIG. 9, part A, as well as signal $S_N$ according to FIG. 9. The output signal of multiplier 32 causes the pulsator 20 to perform the aforedescribed functions. By using several plasma parameters, such as the temperature and the density, an even more certain evaluation of the plasma can be achieved, when its emission is optimal for a particular quantitative analysis.

Figure 10:
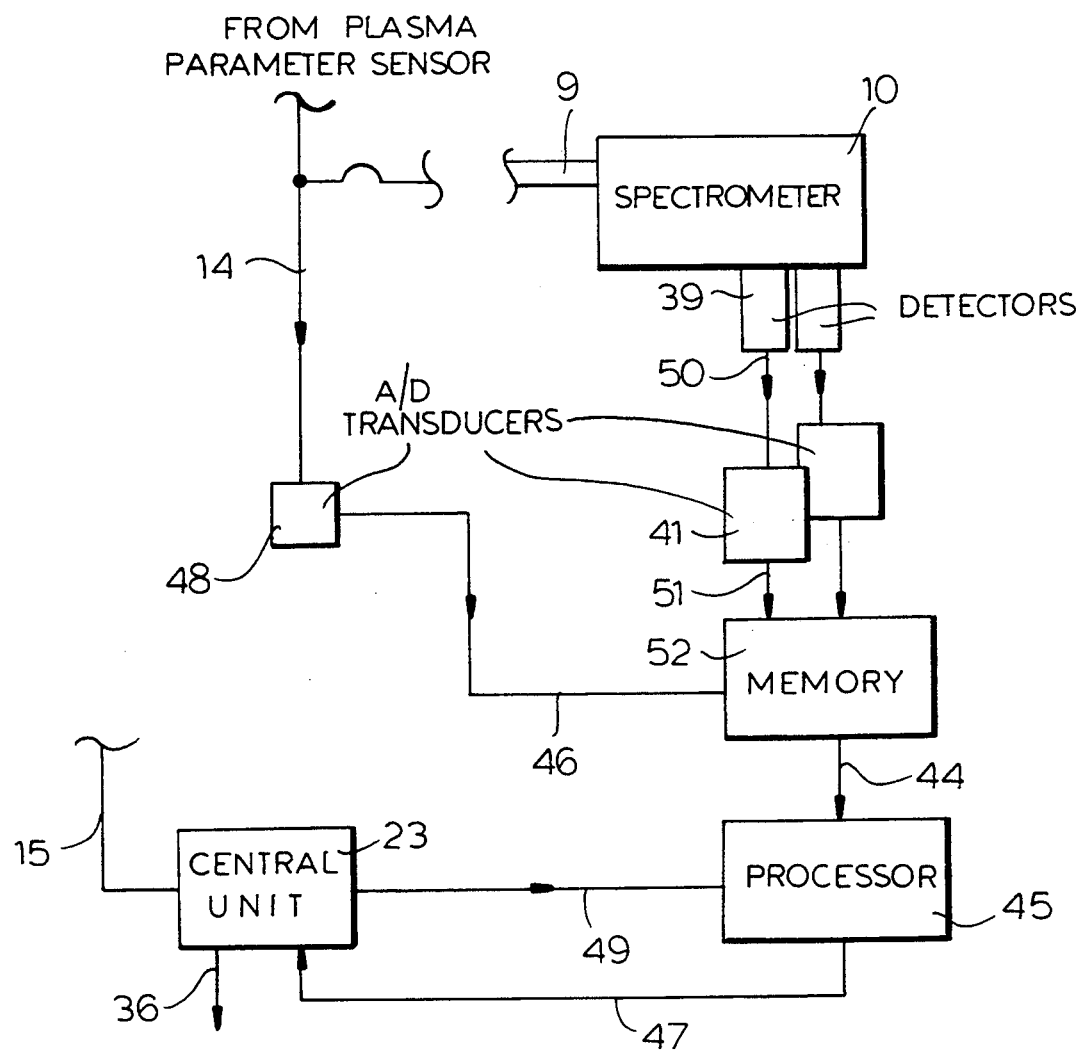
FIG. 10 is a block diagram explaining a procedure in the case of a transfer of a fraction of the found spectrum to the processing unit.

While up to now, especially with reference to FIG. 5, the transfer of the spectrum detected by spectrometer 10 to the processing unit 31 by means of transfer arrangement 11, 12, i.e. by means of an electro-optical shutter 11 with subsequent detector 12 working on a surface and lines base, has been described, FIG. 10 refers particularly to the transfer of a fraction of spectrum of a plasma detected by spectrometer 10. For this purpose at the exit of spectrometer 10, which is not shown in detail, slotted diaphragms are arranged at preselected positions, each of them with a number of subsequent discrete detectors 39. The detectors are positioned so that each of them records a selected element line or a specific background signal. There are at least as many detectors 39 as there are elements to be determined. The band width of the detectors 39 has to be selected so that they can follow the changes undergone in time by the emission. The signals of each detector 39 are directed over lead 50 to the quick A/D transducers 41, from where digital signals of each detector channel passing through lead 51 reach to a memory 52 receiving all digital signals. The memory 52 records the signals in a time-dependent manner.

In order to be able to take into account one or more plasma parameters in the evaluation of the interdependencies recorded in the memory 52, the development in time of the plasma parameter, or of several parameters has to be detected. This happens according to FIG. 10 via lead 14, which applies the signal of the plasma parameter sensor 13 to the A/D transducer 48 which transmits the digitalized time-related curve of plasma parameter for storage in the memory 52, via lead 46. The storage takes place in such a manner that an unequivocal time coordination can be established between the time-related curve of the plasma parameter or of several plasma parameters and the time-related curves of the signals of detectors 39.

The quantitative evaluation of the digitalized time-related curves of plasma parameters and emission intensities for the predetermined emission lines is assumed by the processing unit 45 arranged in sequence after memory 52 via a connection lead 44. From the data stored in memory 52 regarding the development in time of a plasma parameter, for instance T(t), it establishes those time intervals wherein T(t) lies within the predetermined tolerance range $T_1./.T_2$. This function corresponds with those of the comparison unit 17 according to FIG. 5. The predetermined tolerance range $T_1./.T_2$ is taken over by the processing unit 45 from the central unit 23 via lead 49 and is valid for one or more of the predetermined emission lines. After the time intervals are defined, the signals of detectors 39 for these intervals available in memory 52 are inputted in the processing unit 45. The input data are evaluated in the usual manner, for instance by forming line relationships with background correction and the determination of concentration through calibrating curves.

The time-related course of the evaluation can be different. For instance it is possible to perform a timed evaluation after each laser pulse, when stored plasma-parameter data of sensors 13 and detectors 39 are available. They are immediately subsequently evaluated in the above-described manner for the quantitative determination of one element or of several elements, whereby in borderline cases for each of the elements to be defined other predefined limits from one or more plasma parameters are used. The time-dependent evaluation can also be performed after several laser pulses, by storing the signals of sensors 13 and detectors 39 for several pulses and evaluating them only after a predetermined time in the described manner.

The evaluation results are transmitted by the evaluation unit 45 via a lead 47 to the central unit 23, from where they are delivered for instance via lead 36. In addition, the central unit 23 is connected, as previously described, with a control and adjustment unit.

I claim:

1. A method of elemental analysis comprising the steps of:
    (a) directing a laser beam at a material having at least one element for which said material is to be analyzed and with an intensity and for a duration sufficient to generate a plasma at said material emitting spectroscopically detectable radiation including emissions from said element, said laser beam being capable of producing different plasma states in said plasma;
    (b) spectroscopically detecting a spectrum of said radiation, transferring at least a portion of the detected spectrum, decomposing at least said portion of said spectrum to determine said emissions, and analyzing for said element from the determination of said emissions;
    (c) selecting a tolerance range of values for at least one emission-influencing parameter at which said spectrum most accurately represents an analysis of said element;
    (d) monitoring said plasma during the generation thereof for said emission-influencing parameter; and
    (e) transferring at least said portion of said spectrum for determination of said emissions and analysis for said element only upon said emission-influencing parameter falling within said range, and blocking transfer of at least said portion of said spectrum for determination of said emissions and analysis for said element upon said emission-influencing parameter lying above and below said range.

2. The method defined in claim 1 wherein said at least one emission-influencing parameter is a temperature of the plasma.

3. The method defined in claim 1 wherein, in addition to the plasma temperature, a density of the plasma is monitored as an emission-influencing parameter and said spectrum is transferred for determination of said emissions and analysis for said element only upon both of said emission-influencing parameters falling within respective tolerance ranges.

4. The method defined in claim 1, further comprising the step of measuring a maximum value of at least one parameter of said plasma, comparing said maximum value as an actual value with a set-point value range, of varying an energy of pulses of said laser beam to increase an energy of a pulse of said laser beam when said actual value lies below said set-point range and to decrease an energy of a pulse of said laser beam when said actual value is above said set-point range.

5. The method defined in claim 1 wherein a curve of a parameter of the plasma is measured as an actual measurement curve and is compared to an ideal curve of the respective parameter, further comprising the step of determining differences between said curves and controlling an energy of the laser beam continuously in response to the determined differences.

6. The method defined in claim 1 wherein an actual value of a parameter of said plasma is measured and compared with an ideal value specific to at least one element of said material to be analyzed and differences between the actual value and measured value are determined and an energy of said laser beam is controlled in response to the measured differences.

7. The method defined in claim 1 wherein radiation emitted from a common source at said material is directed toward a spectrometer for spectroscopically detecting said spectrum and a sensor effecting monitoring of said plasma.

8. The method defined in claim 1 wherein said material is material of a workpiece produced in a fabrication process, said method further comprising the step of controlling said process in response to said analysis for said element.

9. The method defined in claim 1 wherein emission intensities of a number of predetermined emission lines of the detected spectrum and said emission-influencing parameter are recorded in a time-dependent manner prior to the transfer.

10. An apparatus for elemental analysis, comprising:
a laser directing a laser beam at a material having at least one element for which said material is to be analyzed and with an intensity and for a duration to generate a plasma at said material emitting spectroscopically detectable radiation including emissions from said element;
a spectrometer trained upon said plasma for spectroscopically detecting a spectrum of said radiation, a beam path extending between said plasma and said spectrometer, said spectrometer being provided with means for transferring at least a portion of the detected spectrum, decomposing at least said portion of said spectrum to determine said emissions, and analyzing for said element from said determination of said emissions;
a lens system along said beam path;
a partially transparent mirror in said beam path for directing radiation from said plasma along another path;
a sensor for at least one emission-influencing parameter having a tolerance range of values at which said spectrum most accurately represents an analysis of said element, positioned along said other path for monitoring said plasma during the generation thereof for said emission-influencing parameter;
a laser beam permeable mirror in said beam for shielding said laser against radiation emitted from said plasma; and
means for transferring at least said portion of said spectrum for determination of said emissions and analysis for said element only upon said emission-influencing parameter falling within said range, and blocking transfer of at least said portion of said spectrum for determination of said emissions and analysis for said element upon said emission-influencing parameter lying above and below said range.

11. The apparatus defined in claim 10, further comprising a laser control and adjustment unit connected to said sensor and receiving a predetermined ideal value of said parameter for controlling said laser.

12. The apparatus defined in claim 10 wherein said unit includes a comparator receiving a measured value of said parameter and comparing said measured value with said ideal value.

13. The apparatus defined in claim 12 wherein said sensor is connected to a memory coupled with the spectrometer through a solid diaphragm with respective detectors tuned to respective emission lines.

* * * * *